(12) United States Patent
Link

(10) Patent No.: US 8,062,369 B2
(45) Date of Patent: Nov. 22, 2011

(54) CERVICAL INTERVERTEBRAL PROSTHESIS SYSTEM

(75) Inventor: Helmut D. Link, Hamburg (DE)

(73) Assignee: Cervitech, Inc., San Diego, CA (US)

(*) Notice: Subject to any disclaimer, the term of this patent is extended or adjusted under 35 U.S.C. 154(b) by 581 days.

(21) Appl. No.: 12/169,480

(22) Filed: Jul. 8, 2008

(65) Prior Publication Data

US 2008/0269905 A1    Oct. 30, 2008

Related U.S. Application Data

(63) Continuation of application No. 10/687,933, filed on Oct. 20, 2003, now Pat. No. 7,628,813.

(51) Int. Cl.
*A61F 2/44* (2006.01)

(52) U.S. Cl. .................................. 623/17.11

(58) Field of Classification Search ............... 623/17.11, 623/17.14, 17.15, 17.16, 18.11, 23.47, 23.48; 606/60, 90, 105, 246–249, 257, 279
See application file for complete search history.

(56) References Cited

U.S. PATENT DOCUMENTS

| | | |
|---|---|---|
| 1,174,757 A | 3/1916 | Packer |
| 3,154,072 A | 10/1964 | Mack |
| 4,384,372 A | 5/1983 | Rector |
| 4,627,109 A | 12/1986 | Carabelli et al. |
| 4,759,766 A | 7/1988 | Buettner-Janz et al. |
| 4,782,535 A | 11/1988 | Yewer, Jr. et al. |
| 4,968,027 A | 11/1990 | Anderson |
| 5,036,864 A | 8/1991 | Yewer, Jr. |
| 5,046,488 A | 9/1991 | Schiek, Sr. |
| 5,086,758 A | 2/1992 | Schiek, Sr. et al. |
| 5,172,454 A | 12/1992 | Martignago et al. |
| 5,178,163 A | 1/1993 | Yewer, Jr. |
| 5,269,050 A | 12/1993 | Yewer, Jr. |
| 5,306,309 A | 4/1994 | Wagner et al. |
| 5,316,022 A | 5/1994 | Schiek, Sr. |
| 5,388,274 A | 2/1995 | Glover et al. |
| 5,401,269 A | 3/1995 | Buttner-Janz et al. |
| 5,416,952 A | 5/1995 | Dodge |
| 5,425,773 A | 6/1995 | Boyd et al. |
| 5,432,951 A | 7/1995 | Yewer, Jr. |
| 5,445,601 A | 8/1995 | Harlow |
| 5,470,000 A | 11/1995 | Munoz |
| 5,500,959 A | 3/1996 | Yewer, Jr. |
| 5,507,816 A | 4/1996 | Bullivant et al. |
| 5,534,029 A | 7/1996 | Shima et al. |

(Continued)

FOREIGN PATENT DOCUMENTS

EP    0 955 021    3/1998

(Continued)

OTHER PUBLICATIONS

Japanese Office Action mailed on Jul. 14, 2009 directed at counterpart application No. 2006-534602; 3 pages.

(Continued)

*Primary Examiner* — Eduardo C Robert
*Assistant Examiner* — David Comstock
(74) *Attorney, Agent, or Firm* — NuVasive, Inc.; Jonathan Spangler; Marjorie Jarvis

(57) ABSTRACT

A cervical intervertebral prosthesis system includes prostheses which each have a hinge with a predefined center of hinge movement. To permit better adaptation to the different hinge radii of the cervical intervertebral disks, the cervical intervertebral prostheses of the system include at least two different prostheses with different hinge radii.

10 Claims, 1 Drawing Sheet

U.S. PATENT DOCUMENTS

| | | | |
|---|---|---|---|
| 5,551,085 | A | 9/1996 | Leighton |
| 5,562,738 | A | 10/1996 | Boyd et al. |
| 5,581,810 | A | 12/1996 | Yewer, Jr. |
| 5,745,959 | A | 5/1998 | Dodge |
| 5,895,428 | A | 4/1999 | Berry |
| 6,039,763 | A | 3/2000 | Shelokov |
| 6,053,883 | A | 4/2000 | Schiek, Sr. |
| 6,179,874 | B1 | 1/2001 | Cauthen |
| 6,350,283 | B1 | 2/2002 | Michelson |
| 6,374,464 | B1 | 4/2002 | Lai et al. |
| 6,554,297 | B2 | 4/2003 | Phillips et al. |
| 6,610,089 | B1 | 8/2003 | Liu et al. |
| 2002/0170105 | A1 | 11/2002 | Koene et al. |
| 2004/0078079 | A1 | 4/2004 | Foley |
| 2004/0153157 | A1 | 8/2004 | Keller |

FOREIGN PATENT DOCUMENTS

| | | |
|---|---|---|
| EP | 1 166 725 | 1/2002 |
| FR | 2718635 | 10/1995 |
| JP | 10-234755 | 9/1998 |
| WO | WO-99/11203 | 8/1998 |
| WO | WO-02/080818 | 10/2002 |

OTHER PUBLICATIONS

Link, U.S Office Action mailed on Feb. 3, 2009 directed at U.S. Appl. No. 10/687,933; 5 pages.

Link, U.S Office Action mailed on May 12, 2008 directed at U.S. Appl. No. 10/687,933; 5 pages.

Link, U.S Office Action mailed on Nov. 15, 2007 directed at U.S. Appl. No. 10/687,933; 9 pages.

Link, U.S Office Action mailed on Feb. 12, 2007 directed at U.S. Appl. No. 10/687,933; 10 pages.

Link, U.S Office Action mailed on Jul. 27, 2005 directed at U.S. Appl. No. 10/687,933; 6 pages.

Link, U.S Office Action mailed on Mar. 10, 2005 directed at U.S. Appl. No. 10/687,933; 7 pages.

Link, U.S Office Action mailed on Oct. 5, 2004 directed at U.S. Appl. No. 10/687,933; 4 pages.

Penning, L., (Jun. 1968). "Functional Radiographic Examination," Chapter I of *Functional Pathology of the Cervical Spine*. Excerpta Medica Foundation, New York. Table of Contents, 1-25.

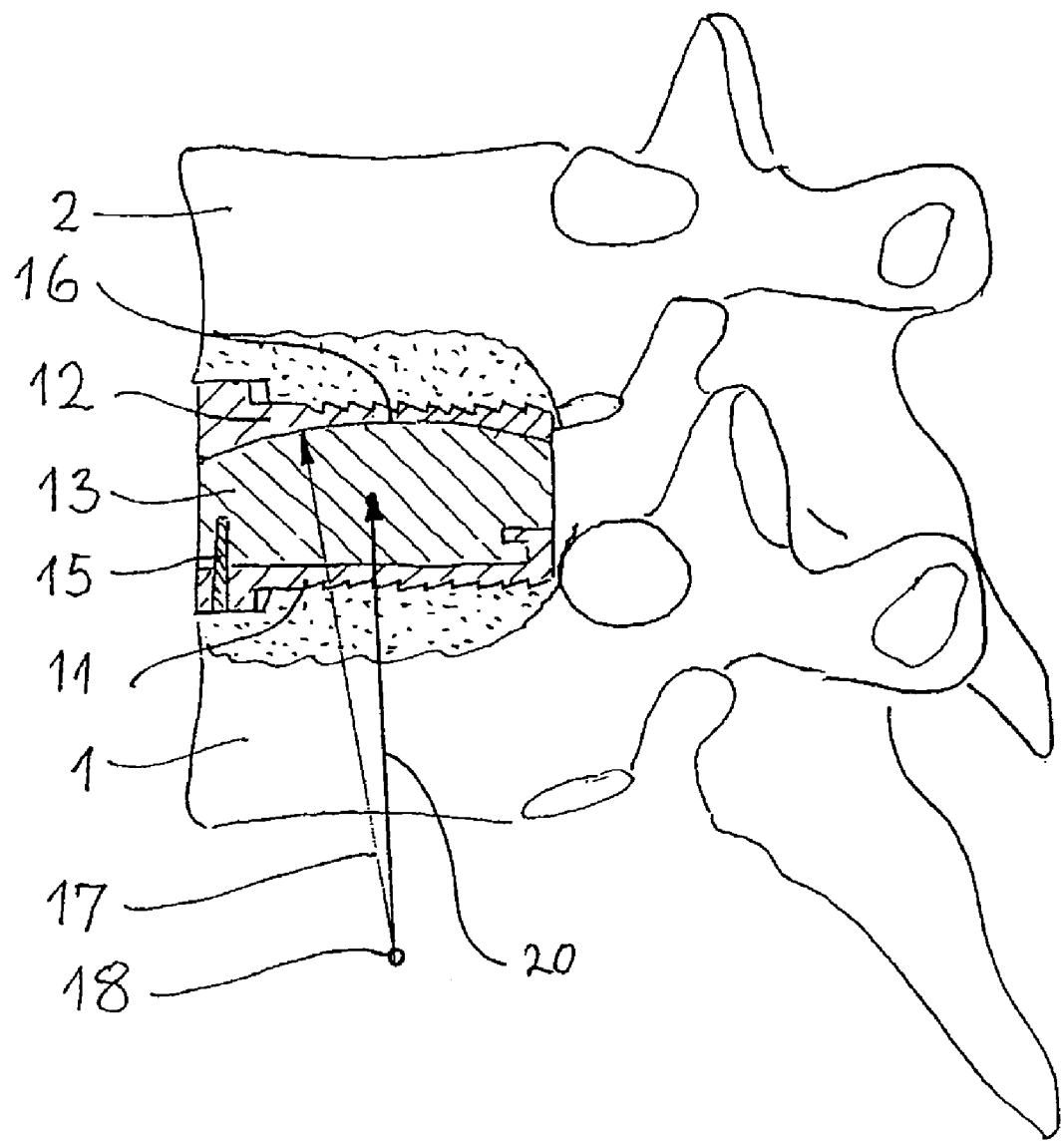

CERVICAL INTERVERTEBRAL PROSTHESIS SYSTEM

This application is a continuation of application Ser. No. 10/687,933, filed Oct. 20, 2003, the entire contents of which are hereby incorporated by reference.

FIELD AND BACKGROUND OF THE INVENTION

The invention relates to cervical intervertebral prostheses which have a predefined center of the hinge movement. In a first known type of such prostheses, the center of the hinge movement is located inside the prosthesis (U.S. Pat. No. 5,425,773; EP-A-1166725). This does not correspond to the natural conditions which the prosthesis is intended to simulate. In another type of intervertebral prosthesis (FR-A-2718635), the hinge is formed by a pair of slide surfaces, the common center of curvature of which lies outside the prosthesis, specifically under it. This approximates to the natural conditions but is still too far remote from them.

SUMMARY OF THE INVENTION

The invention is based on the awareness that the centers of the cervical intervertebral hinge movement are different from vertebra to vertebra (L. Penning: Functional Pathology of the Cervical Spine; Excerpta Medica 1968, pages 1-23). Starting out from this realization, the invention seeks to approximate the prosthetic hinge movement more closely to the natural conditions.

The invention achieves this aim by making available a set of cervical intervertebral prostheses which comprises at least two different prostheses with a different position of the center of the hinge movement. Depending on the position in question, the operating surgeon can select a suitable prosthesis from this set and thus ensure that the movement of the intervertebral joint fitted with the prosthesis is more akin to the natural conditions than was hitherto possible.

This applies especially when the intervertebral prostheses comprise a pair of slide surfaces for forming the hinge. In this case, the two different prostheses differ from one another in terms of the different radii of curvature of their slide surface pairs. According to the invention, a prosthesis intended for a pair of vertebrae lying more in the cranial direction ought to have a greater radius of curvature of its slide surfaces than does a prosthesis which is intended for a pair of vertebrae lying more in the caudal direction.

In some cases it may suffice if the prosthesis set comprises only two prostheses with a different radius of curvature of its slide surfaces, namely a prosthesis with a radius of curvature of its slide surfaces above a defined mean value and a prosthesis with a radius of curvature of its slide surfaces below a defined mean value. This mean value is expediently 18 mm. For example, a set can comprise a first prosthesis with a radius of curvature of its slide surfaces of 22 mm and another prosthesis with a radius of curvature of its slide surfaces of 14 mm. It is desirable to have a larger number of prostheses with a different slide surface radius, for example the set cited in the example just cited can be supplemented by a prosthesis with a slide surface radius of 18 mm and if appropriate a further prosthesis with a slide surface radius of 10 mm.

The invention also relates to a method for determining which intervertebral prosthesis from a plurality of intervertebral prostheses with different hinge radius is suitable for replacing a cervical intervertebral disk. This method is distinguished in that the hinge radius of the affected joint is determined and a prosthesis with a hinge radius approximating to this hinge radius is selected. In this context, the hinge radius is to be understood as the distance between the center of the hinge movement and the midpoint of the prosthesis. The method can be implemented by the physician. However, because of the existing damage, the physician will in general no longer be able to determine the movement characteristics of the joint that is to be replaced. He will therefore rely on the manufacturer of the prostheses carrying out suitable tests, whose results can also subsequently be consulted in the literature, and on said manufacturer then assigning the available prostheses, which are put together in sets, to specific intervertebral spaces. The table below shows an example of how the radii of curvature of the slide surfaces are assigned to the individual intervertebral spaces within defined size ranges (in millimeters).

| Intervertebral space | "Large" series | "Medium" series | "Small" series |
| --- | --- | --- | --- |
| C2/C3 | 22 | 20 | 18 |
| C3/C4 | 22 | 18 | 18 |
| C4/C5 | 18 | 18 | 16 |
| C5/C6 | 18 | 14 | 14 |
| C6/C7 | 14 | 14 | 12 |

As regards the use of small radii of curvature, it should be noted that here too the hinge center lies outside the prosthesis.

BRIEF DESCRIPTION OF THE DRAWING

The sole FIGURE of the drawing depicts an illustrative embodiment to explain the terms used above.

DETAILED DESCRIPTION OF THE INVENTION

An intervertebral prosthesis made up of a lower cover plate 11, an upper cover plate 12 and a prosthetic core 13 is fitted between the vertebral bodies 1 and 2. The prosthetic core 13 is held securely on the lower cover plate 11 by an undercut ledge 14, running along three sides of the prosthesis, and by a catch 15. With the upper cover plate 12, it forms a spherical slide surface pair 16 having a slide surface radius 17 and a center of curvature 18 which forms the center of movement of the hinge formed by the prosthesis. This means that the cover plates 11, 12 and the vertebrae 1, 2 connected to them are able to execute a relative movement with respect to one another which represents a rotation movement about the center 18 as long as the slide surface pair 16 alone determines the relative movement. In practice, other slide surfaces, namely the articular facets, are also involved in determining the relative movement, so that the relative movement actually taking place may deviate a little from this. It will however be appreciated that the hinge movement is all the more harmonious, and continuation of the patient's symptoms all the more unlikely, the more the center 18 of the hinge movement defined by the prosthesis agrees with the natural center of movement. The hinge radius is defined independently of the slide surface radius and differs from the latter in that it is measured from the center 18 of the hinge movement to the geometric midpoint of the prosthesis.

The prostheses intended for the more cranial intervertebral spaces (in particular C2/C3 and C3/C4) are distinguished on the one hand by a larger hinge radius than in the prostheses which are intended for the more caudal intervertebral spaces (in particular C5/C6 and C6/C7). On the other hand, the prostheses to be fitted more in the cranial direction can have a smaller surface extent in particular in the AP direction (AP=anteroposterior) than the prostheses to be fitted more in the caudal direction can. Thus, a further characteristic feature of the invention lies in the fact that the set of intervertebral prostheses comprises at least one first prosthesis whose hinge radius is greater and whose surface extent (in particular in the AP direction) is smaller than those of a second prosthesis.

The invention claimed is:

1. An intervertebral prosthesis system comprising:
   a first prosthesis for replacement of a first intervertebral disk having a first hinge with a pair of slide surfaces having a first radius of curvature, the first intervertebral disk lying in a cranial direction relative to a second intervertebral disk; and
   a second prosthesis for replacement of the second intervertebral disk having a second hinge with a pair of slide surfaces having a second radius of curvature, the second intervertebral disk lying in a caudal direction relative to the first intervertebral disk,
   wherein the first radius of curvature is greater than the second radius of curvature and the first prosthesis has a smaller extent in an anterior-posterior direction than an extent in an anterior-posterior direction of the second prosthesis.

2. The intervertebral prosthesis system according to claim 1, wherein the slide surface radius of the first prosthesis is 18 mm or more and the slide surface radius of the second prosthesis is 18 mm or less.

3. The intervertebral prosthesis system according to claim 1, wherein the slide surface radius of at least one of the first prosthesis and second prosthesis is below 20 mm.

4. The intervertebral prosthesis system according to claim 1, wherein the slide surface radius of the first prosthesis ranges between 22 mm and 18 mm and the slide surface radius of the second prosthesis ranges between 18 mm and 12 mm.

5. The intervertebral prosthesis system according to claim 1, wherein the slide surface radius of the first prosthesis is 20 mm or more and the slide surface radius of the second prosthesis is 20 mm or less.

6. A cervical intervertebral prosthesis system comprising:
   a first prosthesis for replacement of a first intervertebral disk having a first hinge with a pair of slide surfaces having a first radius of curvature, the first intervertebral disk lying in a cranial direction relative to a second intervertebral disk; and
   a second prosthesis for replacement of the second intervertebral disk having a second hinge with a pair of slide surfaces having a second radius of curvature, the second intervertebral disk lying in a caudal direction relative to the first intervertebral disk,
   wherein the first radius of curvature is greater than the second radius of curvature and the first prosthesis has a smaller extent in an anterior-posterior direction than an extent in an anterior-posterior direction of the second prosthesis.

7. The cervical intervertebral prosthesis system according to claim 6, wherein the slide surface radius of the first prosthesis is 18 mm or more and the slide surface radius of the second prosthesis is 18 mm or less.

8. The cervical intervertebral prosthesis system according to claim 6, wherein the slide surface radius of at least one of the first prosthesis and the second prosthesis is below 20 mm.

9. The cervical intervertebral prosthesis system according to claim 6, wherein the slide surface radius of the first prosthesis ranges between 22 mm and 18 mm and the slide surface radius of the second prosthesis ranges between 18 mm and 12 mm.

10. The cervical intervertebral prosthesis system according to claim 6, wherein the slide surface radius of the first prosthesis is 20 mm or more and the slide surface radius of the second prosthesis is 20 mm or less.

* * * * *